United States Patent [19]
Bednarek

[11] Patent Number: 5,785,706
[45] Date of Patent: Jul. 28, 1998

[54] NONSURGICAL MAPPING AND TREATMENT OF CARDIAC ARRHYTHMIA USING A CATHETER CONTAINED WITHIN A GUIDING INTRODUCER CONTAINING OPENINGS

[75] Inventor: Michael C. Bednarek, Minnetonka, Minn.

[73] Assignee: Daig Corporation, Minnetonka, Minn.

[21] Appl. No.: 751,303

[22] Filed: Nov. 18, 1996

[51] Int. Cl.⁶ .................................................. A61B 17/39
[52] U.S. Cl. .......................... 606/41; 600/372; 600/373; 600/374; 607/119; 607/122
[58] Field of Search .............................. 128/639, 642, 128/772; 606/41; 607/119, 122; 600/372, 373, 374

[56] References Cited

U.S. PATENT DOCUMENTS

| | | | |
|---|---|---|---|
| 5,154,387 | 10/1992 | Trailer | 128/642 |
| 5,279,299 | 1/1994 | Imran | 128/642 |
| 5,348,554 | 9/1994 | Imran et al. | 607/122 |
| 5,549,581 | 8/1996 | Lurie et al. | 128/642 |
| 5,578,067 | 11/1996 | Ekwall et al. | 128/642 |
| 5,607,462 | 3/1997 | Imran | 607/122 |

Primary Examiner—Lee S. Cohen
Assistant Examiner—David M. Ruddy
Attorney, Agent, or Firm—Scott R. Cox

[57] ABSTRACT

A process for the treatment of cardiac arrhythmia by use of ablation and/or mapping procedures comprising ablating discrete ablation tracks within the heart by use of a guiding introducer containing openings with an ablation catheter. Also disclosed is the shape and structure of the guiding introducer containing openings to be used for the ablation procedure.

19 Claims, 4 Drawing Sheets

NONSURGICAL MAPPING AND TREATMENT OF CARDIAC ARRHYTHMIA USING A CATHETER CONTAINED WITHIN A GUIDING INTRODUCER CONTAINING OPENINGS

BACKGROUND OF THE INVENTION

1. Field of Invention

This invention relates to a process for the treatment of cardiac arrhythmia using a catheter contained within a guiding introducer containing openings. In addition, it relates to a preferred structure for the guiding introducer containing openings which is used with a mapping or ablation catheter for the treatment of cardiac arrhythmia.

2. Prior Art

Introducers and catheters have been in use for medical procedures for many years. For example, one use is to convey an electrical stimulus to a selected location within the human body. Another use is to monitor and make measurements for diagnostic tests within the human body. Thus, catheters may examine, diagnose and treat while positioned at a specific location within the body which is otherwise inaccessible without more invasive procedures. In use, catheters may be inserted into a vein or artery which is near the body surface. These catheters are then guided to a specific location for examination, diagnosis or treatment by manipulating the catheter through the artery or vein of the human body.

Catheters have become increasingly useful in remote and difficult to reach locations within the body. However, the utilization of these catheters is frequently limited because of the need for precise placement of the electrodes of the catheter at a specific location within the body.

Control of the movement of catheters to achieve such precise placement is difficult because of the inherent structure of the catheter. The body of a conventional catheter is long and tubular. To provide sufficient control of the movement of the catheter, it is necessary that its structure be somewhat rigid. However, the catheter must not be so rigid as to prevent the bending or curving that is necessary for movement of the catheter through the vein, artery or other body part to arrive at the specified location. Further, the catheter must also not be so rigid as to cause damage to the vasculature while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through a vein or artery and then is positioned at a specified location within the heart. Typically, the catheter is inserted in an artery or vein in the leg, neck, upper chest or arm of the patient and threaded, often with the aid of a guidewire or introducer, until the tip of the catheter reaches the desired location in the heart.

A new procedure used for treatment of certain cardiac problems in general and cardiac arrhythmia in particular within the last 10 to 15 years is catheter ablation. This procedure has been used to interrupt or modify existing conduction pathways associated with arrhythmia within the heart. The particular area for ablation depends on the type of underlying arrhythmia. One common ablation procedure is the treatment of atrioventricular (AV) nodal reentrant tachycardia. With this problem ablation of the fast or slow AV nodal pathways has become an accepted treatment. See Singer, I., et al., "Catheter Ablation for Arrhythmias" *Clinical Manual of Electrophysiology*. pp. 421–431 (1993); Falk, R. H., et al., *Atrial Fibrillation Mechanisms in Management*, pp. 359–374 (1992); Horowitz, L. N., *Current Management of Arrhythmias*, pp. 373–378 (1991); and Martin, D., et al., *Atrial Fibrillation*, pp. 42–59 (1994).

The use of ablation catheters for ablating discrete locations within the heart has been disclosed, for example in U.S. Pat. Nos. 4,641,649, 5,263,493, 5,231,995, 5,228,442 and 5,281,217.

Ablation catheters have also been designed whereby the electrodes are recessed inside the outer surface of the catheter. For example, U.S. Pat. No. 5,456,254 discloses an ablation catheter whereby openings for the electrodes are provided in the outer surface of the flexible, elongated catheter assembly. A similar structure for an ablation catheter is disclosed, for example, in FIG. 32 of U.S. Pat. No. 5,499,981. See also U.S. Pat. No. 5,425,364.

Ablation of a precise location within the heart requires precise placement within the heart of the ablating electrodes of the ablation catheter. Precise positioning is especially difficult within a human heart because of its physiology and because ablation procedures normally occur while the heart is beating. Conventionally, placement of an ablation catheter was accomplished using a combination of electrophysiological guidance and fluoroscopy (placement of the catheter in relation to known features of the heart which are marked by radiopaque diagnostic catheters).

In order to achieve more precise placement of an ablation catheter, a new ablation procedure involving the use of a shaped, precurved guiding introducers has been developed.

A system comprising a shaped sheath and a steerable catheter for ablation procedures in the heart is disclosed in FIGS. 20–23 of U.S. Pat. No. 5,476,495. In addition, U.S. Pat. No. 5,575,766 discloses a process for the nonsurgical mapping and treatment of atrial arrhythmia using a series of shaped guiding introducers. In this process, an ablation catheter is inserted within the lumen of the shaped guiding introducer. The particular shape of the guiding introducer is chosen to direct the ablation catheter to the specific location within the heart for the ablation treatment. However, once the guiding introducer is in place, the distal tip of the ablation catheter, which contains the ablation electrodes, is extended away from the distal tip of the guiding introducer. These electrodes then contact the inner surface of the heart to perform the mapping or ablation procedures. While the shape of the guiding introducer is critical to the successful performance of these procedures, as their shape guides the ablation catheter to the precise location necessary for the ablation procedure, the ablation electrodes still must be extended from the distal tip of the guiding introducer to perform the ablation procedure. The '766 patent also discloses that treatment of atrial fibrillation requires the formation of linear lesions on the inside surface of the heart.

In addition to the guiding introducers disclosed by U.S. Pat. No. 5,575,766, other shaped guiding introducers for guiding ablation catheters to particular locations within the heart have been disclosed in U.S. Pat. No. 5,427,119, 5,497,774 and 5,564,440. Each of these guiding introducers are useful in performing ablation procedures at specific locations within the heart. However, to perform these ablation procedures, the distal end of the ablation catheter containing its electrode must again be extended away from the distal end of the guiding introducer. To perform the ablation procedure, the electrodes of the catheter are drawn across the cardiac tissue.

Many ablation procedures now require the formation of a linear track or lesion during the ablation procedure. U.S. Pat. No. 5,487,385 discloses a system for creating linear lesions in the right atrial chamber of the heart. The system of the '385 patent utilizes a generally straight, hollow sheath (22) and an ablation catheter (32) contained within the lumen of the sheath. To perform the ablation procedure a portion of the distal tip of the ablation catheter extends out from the sheath through an opening (30). All ablation procedures occur while the ablation catheter is extended outside the body of the sheath. See, for example, FIGS. 1, 3, 5, 6 and 7.

Even when shaped guiding introducers, such as those disclosed above are used in an ablation procedure, formation of an adequate linear lesion may not be easy because it is difficult to maintain the ablating electrodes of the ablation catheter at the precise location necessary for the ablation procedure for a sufficient period of time. This is especially true because the heart is beating throughout the procedure. Even skilled electrophysiologists now mandate that the location selected for the ablation procedure be ablated multiple times to assure formation of an adequate linear lesion.

For all these reasons it is necessary for improvements in medical devices used to direct ablation catheters to the correct location within the heart for mapping and ablation procedures.

Accordingly, it is an object of this invention to disclose a process for the treatment of cardiac arrhythmia by the use of an ablation catheter contained within a guiding introducer containing openings.

It is a still further object of this invention to disclose a process for the formation of ablation tracks or linear lesions within the heart using a guiding introducer containing openings as an element of the treatment of cardiac arrhythmia.

It is a further object of this invention to disclose the structure of a guiding introducer containing openings for electrophysiology procedures for the treatment of cardiac arrhythmia.

It is a still further object of the invention to disclose the structure for a guiding introducer containing openings for use with an ablation catheter for the mapping and ablation of locations within the heart.

It is a still further object of this invention to disclose a guiding introducer containing openings which is utilized with an ablation catheter to form linear ablation tracks or lesions within the heart.

It is a further object of this invention to disclose a guiding introducer containing openings into which an ablation catheter is inserted, whereby the ablation catheter ablates cardiac tissue while the ablation catheter remains within the lumen of the guiding introducer containing openings.

It is a still further object of this invention to disclose a system for linear ablation comprising a guiding introducer containing openings and an ablation catheter, wherein the ablating electrodes of the ablation catheter are retained within the lumen of the guiding introducer containing openings during the ablation procedure.

It is a still further object of this invention to disclose a process for the nonsurgical treatment of cardiac arrhythmia using an ablation catheter and a guiding introducer containing openings, wherein the ablation catheter is retained within the lumen of the guiding introducer during the treatment and wherein the guiding introducer containing openings is utilized with the ablation catheter to form a linear ablation track or lesion.

These and other objects can be obtained by the disclosed process for the treatment of cardiac arrhythmia and the design of the guiding introducer containing openings for use with that process which are disclosed by the instant invention.

SUMMARY OF INVENTION

The instant invention includes a process for the nonsurgical mapping and treatment of cardiac arrhythmia using an ablation catheter and a guiding introducer containing openings comprising:

- introducing into the heart a guiding introducer containing openings wherein the guiding introducer containing openings contains a lumen and a series of openings,
- introducing into the lumen of the guiding introducer containing openings a catheter for ablating or mapping cardiac tissue containing one or more ablation electrodes,
- extending the electrodes of the ablation catheter into the distal end of the lumen of the guiding introducer containing openings such that one or more of the electrodes align with at least a portion of one or more of the openings of the guiding introducer containing openings,
- ablating cardiac tissue through the openings in the guiding introducer containing openings and
- repeating the ablation procedure as necessary through the openings of the guiding introducer containing openings to form a linear lesion in the heart.

The instant invention also discloses a structure for the guiding introducer containing openings comprising a first and second section wherein the first section is a generally hollow, elongated introducer section, wherein the second section contains a plurality of openings, wherein the openings are generally contained within a longitudinal line extending downward through a portion of the second section and wherein the openings are of sufficient size to permit ablation of cardiac tissue by an electrode of the ablation catheter through the openings of the guiding introducer with openings.

In addition, the instant invention discloses a system for producing linear ablation tracks in cardiac tissue inside the heart comprising a guiding introducer containing openings and an ablation catheter, wherein the structure of the guiding introducer containing openings is as described above.

DETAILED DESCRIPTION OF THE PREFERRED EMBODIMENT

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve contained within the atrioventricular septum communicates the right atrium with the right ventricle. On the inner wall of the right atrium where it is connected with the left atrium is a thin walled, recessed portion, the fossa ovalis. Between the fossa ovalis and the tricuspid valve is the opening or ostium for the coronary sinus. The coronary sinus is the large epicardial vein which accommodates most of the venous blood which drains from the myocardium into the right atrium.

In the normal heart, contraction and relaxation of the heart muscle (myocardium) takes place in an organized fashion as electro-chemical signals pass sequentially through the myocardium from the sinoatrial (SA) node to the atrioventricular (AV) node and then along a well defined route which includes the His-Purkinje system into the left and right ventricles. Initial electric impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as cardiac arrhythmia. It is sometimes difficult to isolate a specific pathological cause for these arrhythmias although it is believed that the principle mechanism for many is one or a multitude of reentry circuits. Efforts to alleviate the effect of these arrhythmia in the past have included significant usage of pharmacological treatments. While pharmacological treatments are sometimes effective, in some circumstances drug therapy has been ineffective and frequently is plagued with side effects such as dizziness, nausea, vision problems and other difficulties.

In the past, surgical procedures have also been utilized in the treatment of some atrial arrhythmia. The goal of these surgical procedures parallels that of the pharmacological treatments, to relieve the subjective symptoms of arrhythmia as well as to normalize hemodynamics. For example, one method suggested for treatment of atrial fibrillation requires isolation of the left atrium from the remainder of the heart by a surgical procedure. See Cox, J. L., et al., "The Surgical Treatment of Atrial Fibrillation," *J. Thoracic and Cardiovascular Surgery*, Vol. 101, No. 4, p. 570 (1991). The initial incisions followed by the scar tissue left by such surgery effectively isolates the left atrium and, in some cases, provides relief for the patient. Such relief can occur as long as the right atrium maintains adequate sinus rhythm. Various problems associated with this procedure, other than the maintenance of appropriate sinus rhythm, include thromboembolic risks.

Another procedure for treatment of atrial arrhythmia involves ablating the His bundle. A permanent pacemaker is then installed, resulting in a regular ventricular beat. See Cox, J. L., et al., "The Surgical Treatment of Atrial Fibrillation," *Journal of Thoracic and Cardiovascular Surgery*, Vol. 101, No. 4, pp. 570–572 (1991). However, because the atria may continue to fibrillate, normal cardiac hemodynamics are not restored and there is still vulnerability to thromboembolism.

A more complex surgical procedure, the "Maze" procedure, has also been designed to treat atrial arrhythmia. See Cox, J. L., et al., "The Surgical Treatment of Atrial Fibrillation," *Journal of Thoracic and Cardiovascular Surgery*, Vol 101 pp. 569–83 (1989). During this procedure appropriately placed atrial incisions interrupt the conduction routes of those areas in the atria that produce the most common reentrant circuits. The procedure is also designed to direct the sinus impulse from the sinus node to the AV node along a specified route. After the procedure, the entire atrial myocardium (except for the atrial appendages and pulmonary veins) is designed to be electrically active by providing for multiple blind alleys off the main conduction route between the SA node and the AV node, thereby preserving atrial transport function postoperatively. While this procedure has resulted in successful treatments for certain patients, there are significant risks present due to the extensive nature of the surgery.

The effectiveness of the "Maze" procedure is dependent upon the destruction of cardiac tissue within the atrium along specific lines or tracks to prevent the formation of reentry circuits while still allowing the atria to contract and permitting the return of normal atrio-ventricular conductivity. It has been discovered that similar success can be achieved without invasive surgery by the use of ablation procedures. These ablation procedures have been effective in the atria of the heart. However, to accomplish these procedures the ablation catheter must be positioned at predetermined locations to ablate predetermined tracks within the heart, thus forming a natural barrier to the formation of the reentry circuits. In addition to the necessity of producing ablation tracks or linear lesions in well defined areas of the heart, it is also critical for proper transmural lesion formation that adequate contact pressure be maintained between the ablation catheter electrode and the heart tissue to be ablated. The formation of such linear tracks is disclosed in U.S. Pat. No. 5,575,766.

The ablation catheters used to perform these ablation procedures produce scar tissue at the ablation site within the heart. The energy necessary to scar or ablate the tissue can be provided by a number of different sources. Originally, direct current was utilized to provide the energy for ablation procedures. Laser, microwave, ultrasound, radio frequency and fulgutronization procedures have also been utilized to perform ablation procedures. However, the preferred source of energy for the ablation procedures is radio frequency energy.

Mere introduction of an ablation catheter into the heart without precise placement of the ablation electrode at the correct location and consistent pressure on the cardiac tissue will not be sufficient to form the desired ablation tracks or lesions. This precise placement and contact pressure has been produced using specialized precurved guiding introducers to guide the ablation catheter to specific location in the heart and to permit adequate pressure to be placed on the ablation electrode of the ablation catheter to produce an adequately ablated track or lesions in U.S. Pat. Nos. 5,427,119, 5,497,774, 5,575,766 and 5,564,440. However, even when using these guiding introducers, production of adequate linear lesions or tracks in the heart may be difficult because these guiding introducers require that the ablating electrodes of the ablation catheter be extended from the distal tip of the guiding introducer. The greater distance that the ablation electrode of the ablation catheter is extended from the distal tip of the guiding introducer, the more likely that problems will occur in the formation of the adequate linear ablation tracks or lesions in cardiac tissue.

Medical practitioners often monitor the introduction of cardiac catheters and their progress through the vascular system by use of fluoroscopes. Unfortunately, fluoroscopes can not easily identify specific features in the heart, thus making accurate placement and utilization of ablation catheters extremely difficult. Accurate placement is especially difficult as the beating heart is in motion, resulting in the catheter moving within the heart as blood is being pumped through the heart.

The guiding introducers containing openings of this invention address these problems by positioning the mapping and/or ablation catheter at the precise location necessary for the ablation procedure. In addition, the guiding introducer containing openings permits the ablation catheter to ablate cardiac tissue while restrained within the lumen of the guiding introducer containing openings without moving the guiding introducer containing openings itself.

The guiding introducer containing openings used for the ablation procedure permits the ablation catheter to move within the guiding introducer containing openings, thus allowing the ablation electrode to create an ablation track without moving the guiding introducer once it is properly positioned. With the guiding introducer containing openings holding the ablation catheter in a fixed location, the ablation catheter then ablates the cardiac tissue to form the ablation track or lesion. More than one passage over a track generally will be necessary to completely ablate the cardiac tissue. These multiple passes are also made easier by use of the guiding introducer containing openings.

When conventional guiding introducers such as those disclosed in U.S. Pat. No. 5,575,766 are utilized, the distal tip of the ablation catheter must be extended from the distal tip of the guiding introducer to perform the ablation procedure. In this situation, the ablation electrodes may move from the desired ablation track during the procedure as a result of the movement of the cardiac tissue during the beating of the heart. In addition, the movement of blood within the chamber of the heart may also adversely affect the precise placement of the electrodes of the ablation catheter. These problems are alleviated by restraining the ablation catheter within the lumen of the guiding introducer containing openings.

The specially designed guiding introducer containing openings is produced from conventional elongated introducers. Although the guiding introducer containing openings is described as having a pair of sections, preferably, it is produced in a conventional introducer production procedure, formed into a single unitary structure.

Additional features of this guiding introducer containing openings other than its unique shape include radiopaque tip markers and vents which will be discussed in more detail later.

The guiding introducer containing openings for use with an ablation catheter (10) is preferably divided into two sections (12, 14). See FIG. 1. The first section (12) of this guiding introducer containing openings is a conventional, generally elongated, hollow straight introducer section of sufficient length for introduction into the patient and for manipulation from the point of insertion to the specific desired location within the heart.

Merged with the distal end of the first section of this guiding introducer containing openings is the second section (14) which forms the portion of the guiding introducer containing the openings. The shape of these openings (16) is not particularly critical. For example, they may be circular openings or extended slots which are longer than they are wide. See FIGS. 1, 2 and 3.

The openings (16) of this second section are preferably aligned in a longitudinal line running to or near the distal tip of the guiding catheter containing openings. A number of individual openings in this section are provided, preferably from about 3 to about 100 individual openings. The number of openings is dependent upon a number of factors, including the size and shape of the individual openings. The overall length of the second section of the guiding introducer containing openings which contains these openings is generally from about 5 to 8 centimeters in length. Extending the openings proximal from the distal tip of the guiding introducer containing openings beyond this distance is not practical because the structure of the guiding introducer containing openings would be weakened substantially. In addition, ablation tracks or lesions greater in length than about 7 centimeters are not necessary.

In a preferred embodiment, the openings must be sufficiently large to permit an electrode (20) of the ablation catheter (18) which is located against that opening to contact the cardiac tissue with sufficient pressure to create a lesion. See FIG. 8. However, the openings must not be so large as to allow the catheter (18) to extend out through any of the openings of the guiding introducer containing openings. While physical contact between the ablating electrode and the cardiac tissue is preferred, adequate lesions may be formed as long as one of the openings in the guiding introducer containing openings is placed between the ablating electrode and the cardiac tissue. In this circumstance, a small gap may exist between the ablating electrode and the cardiac tissue, although that gap will not be wider than the thickness of the wall of the guiding introducer containing openings.

In addition, it is not critical that the ablating electrode line up directly with one of the openings. The ablating electrode may, in fact, be aligned with more than one opening with a bridge (21) of introducer material present between the two openings. See FIG. 8. The ablating electrode may extend across the bridge between two openings and still permit an adequate lesion to be formed in the cardiac tissue. The size of the bridge may be made as small as possible as long as structural stability of the guiding introducer containing openings is retained. Thus, the size of the bridge may be larger or smaller depending on the composition of the material of the guiding introducer containing openings. In one embodiment, the width of the bridge using conventional introducer material may be 0.5 millimeter or less. Notwithstanding, as long as the ablating electrode is either directly in contact with or directly adjacent to the cardiac tissue through one of the openings, an adequate ablation lesion can be formed.

Figure 1:
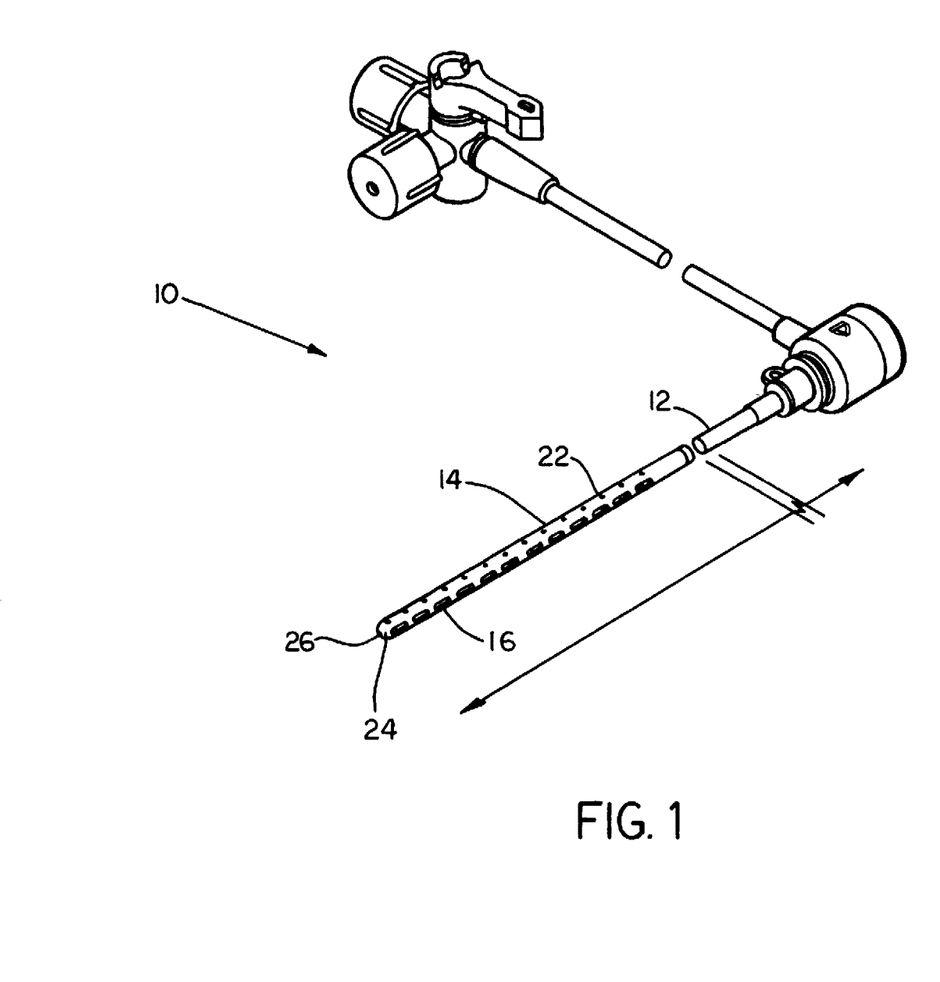
FIG. 1 is a side, elevated cutaway view of the guiding introducer containing openings secured to a valve and side port tubing.
Figures 2, 4, 5:
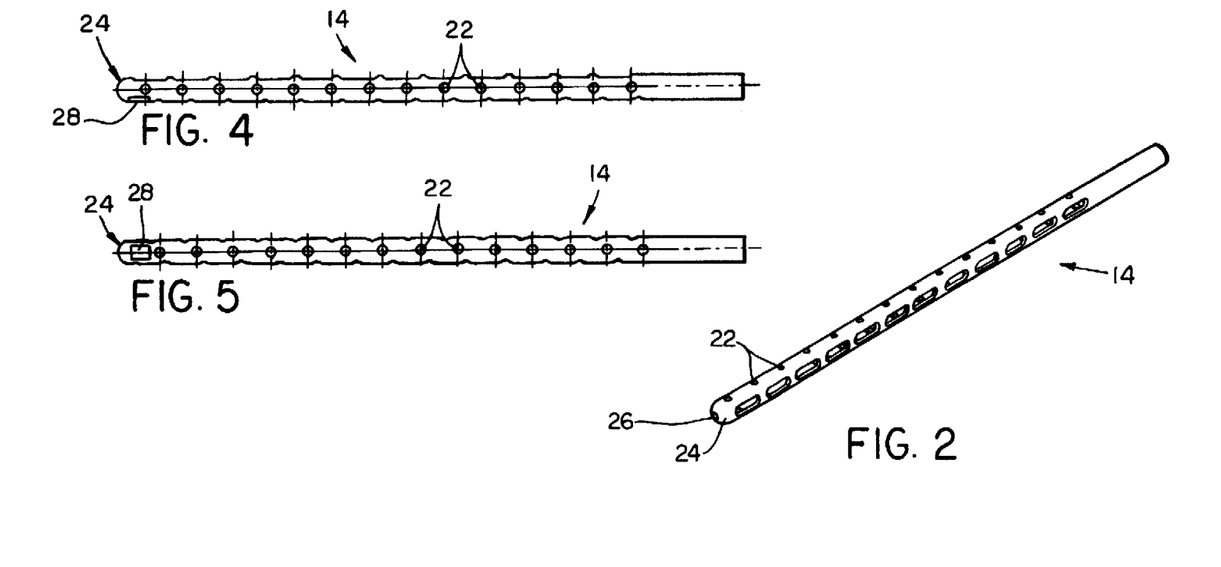
FIG. 2 is a side elevated view of the second section of the guiding introducer containing openings.
FIG. 4 is a top view of the second section of the guiding introducer containing openings rotated 90° clockwise from the position of FIG. 3.
FIG. 5 is a top view of the second section of the guiding introducer containing openings rotated 90° clockwise from the position of FIG. 4.
Figure 3:
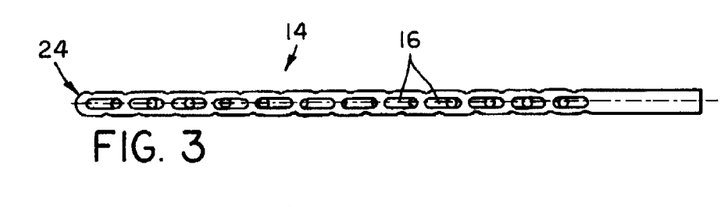
FIG. 3 is a top view of the second section of the guiding introducer containing openings showing the slots of the guiding introducer containing openings.

In a preferred embodiment, these openings are longer than they are wide to form a slot as shown in FIGS. 1, 2 and 3. This structure permits a sufficient exposure of the surface of the electrode to the cardiac tissue while at the same time preventing the electrode from passing outside the guiding introducer through its slots. See FIG. 8. In a preferred embodiment, the length of the slot is from about 3 millimeters to about 10 millimeters. The preferred width of the openings will depend on the size of the ablation electrode of the ablation catheter.

Preferably, the ablation procedures are carried out by the tip electrode (20) of the ablation catheter. In this circumstance, the diameter of the tip electrode is approximately equivalent to the outside diameter of the ablation catheter. The diameter of the ablation catheter must be greater than the width of the opening. Preferably, the widest portion of the opening should be in the range from about 25 to about 90 percent of the diameter of the tip electrode of the ablation catheter and, more preferably, from about 50 to about 90 percent of its diameter.

A conventional tip electrode (20) used with an ablation catheter (18) is generally about 4 millimeters in length. While shorter or longer ablating electrodes may be used with the guiding introducer containing openings, in a preferred embodiment the length of this tip electrode should be at least about 4 millimeters or more.

Figure 6:
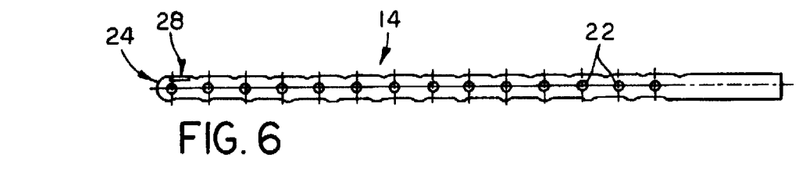
FIG. 6 is a top view of the second section of the guiding introducer containing openings rotated 90° clockwise from the position of FIG. 5.

During the ablation procedures where the ablating electrode of the ablation catheter is contained within the guiding introducer containing openings, there may be significant heat build up. To lessen the effect of this heat buildup, it is important that there be ventilation or liquid cooling of the ablating electrode. This ventilation is preferably produced by means of a series of ventilation apertures (22) within the second section of the guiding introducer containing openings. These apertures permit fluids to flow in and out of the guiding introducer containing openings to cool the ablation electrode or electrodes. One embodiment of these apertures is shown, for example, in FIGS. 2 through 6. Preferably these apertures are relatively small, circular apertures, although size and shape is not particularly critical. In one preferred embodiment, the diameter of these circular apertures (12) is about 0.5 to about 1.5 millimeters. In a preferred embodiment, these apertures (22) are also produced in a series extending down the second section of the guiding introducer containing openings. See, for example, FIGS. 4, 5 and 6. In a more preferred embodiment, three separate linear series of apertures are provided, each series located about 90° axial from each other and the openings of the guiding introducer containing openings.

Figure 7:
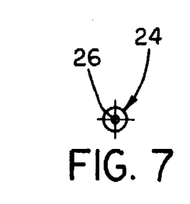
FIG. 7 is an end view of the distal tip of the guiding introducer containing openings.
Figure 8:
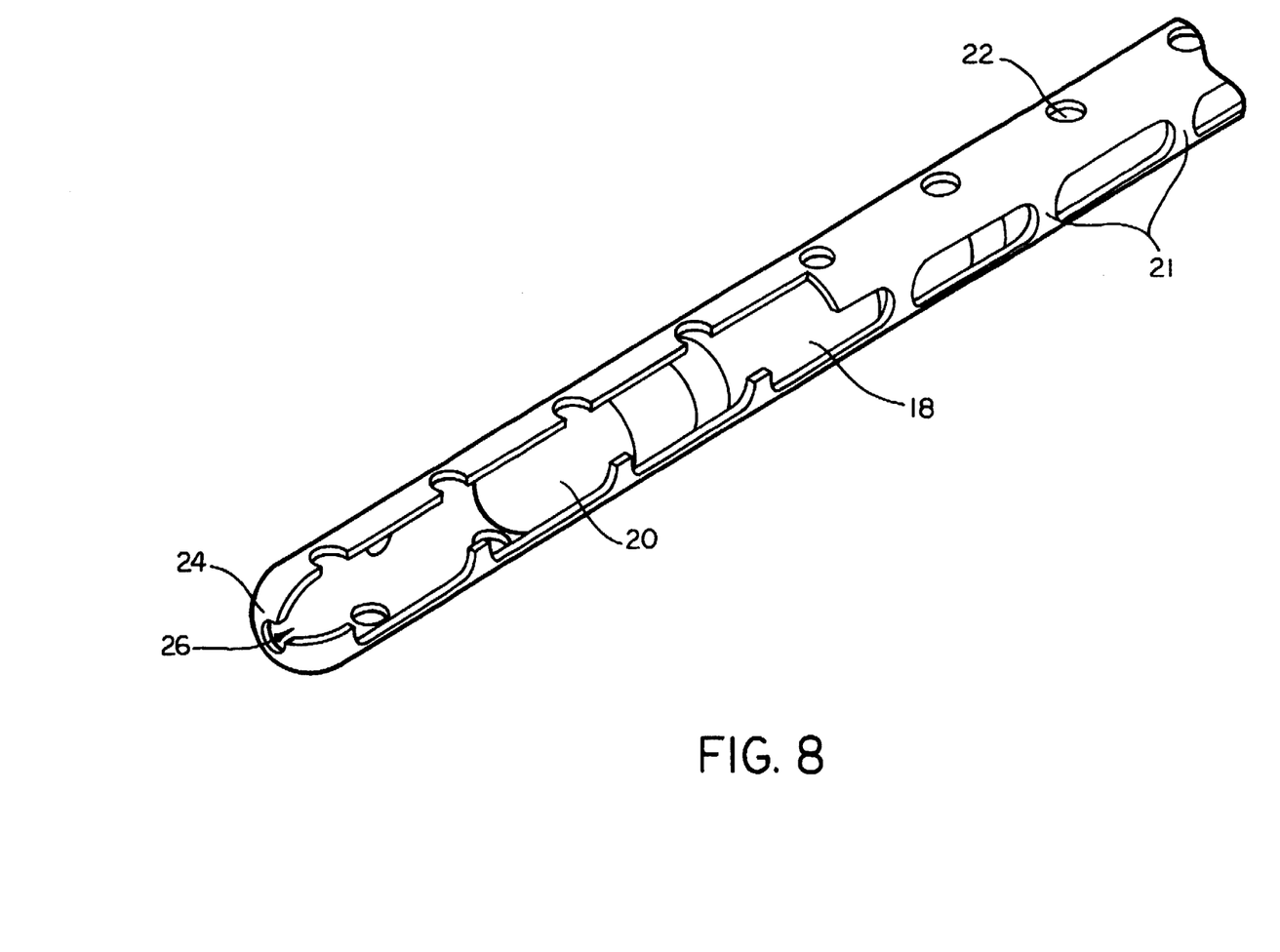
FIG. 8 is a cutaway view of a portion of the distal end of the guiding introducer containing openings showing the distal tip of the ablation catheter contained within the lumen of the guiding introducer.

In a preferred embodiment the distal tip (24) of the guiding introducer containing openings is partially or totally closed to prevent the distal tip from being extended through the distal tip of the guiding introducer containing openings. This structure retains the ablation electrodes of the ablation catheter within the guiding introducer containing openings. Although the distal tip of the guiding introducer containing openings may be completely closed, in a preferred embodiment, a hole (26) is provided in the distal tip (24) as shown in FIGS. 7 and 8. This hole can be any size less than about 90 percent of the diameter of the tip of the ablation catheter. This hole is preferably about the size of one of the ventilation apertures that are provided axial from the openings. The purpose of the hole is to permit blood located outside the guiding introducer containing openings to be drawn into the lumen of the guiding introducer containing openings as the distal tip of the ablation catheter is pulled away from the distal tip of the guiding introducer containing openings. This hole thus provides better ventilation for the ablating tip electrode (20) by permitting blood to be drawn into the lumen of the guiding introducer containing openings.

The outside diameter of the ablation catheter should be approximately the same French size as is the inner diameter of the guiding introducer containing openings. Even when the same French size is utilized however, there is normally a small amount of interior space between the sides of the ablation catheter and the inner wall of the guiding introducer. This space can be used as a conduit to receive injected cooling fluid through the guiding introducer containing openings. In a preferred embodiment, a cooling solution is introduced into the guiding introducer containing openings around the ablation catheter during the ablation procedure. This fluid passes down and around the ablation catheter and cools the ablation catheter during the ablation procedure, thus limiting the likelihood of formation of clots or other coagulum from excess heat buildup during an ablation procedure.

The guiding introducer containing openings preferably also contains one or a multitude of radiopaque tip markers near its distal tip. In a preferred embodiment a single radiopaque tip marker (28) is located near the distal tip of the guiding introducer containing openings. See FIGS. 4, 5 and 6. This radiopaque tip marker performs a unique function because of its location. Instead of a conventional ring tip marker which circles the diameter of the guiding introducer containing openings, in a preferred embodiment, the tip marker is generally square in shape and does not cover more than about 90° of the circumference of the tip of the guiding introducer containing openings, as shown in FIG. 5. Placement of the tip marker (28) in a fixed location assists in the precise positioning of the openings of the guiding introducer containing openings under fluoroscopy. This permits the physician to properly position the guiding introducer containing openings such that the openings are placed against the particular cardiac tissue where the ablation procedure is to be performed.

The guiding introducer containing openings may be made of any material suitable for use in humans which has a memory or permits distortion from, and substantial return to, the desired shape. In a preferred embodiment the first section of the guiding introducer containing openings is preferably braided to provide greater support for the ablation catheter. The distal portion of the guiding introducer containing openings may also be stiffened by means of a number of well recognized methods, such as braiding as long as the braids, if metal, are isolated from the electrodes. Alternatively, if the distal portion is sufficiently stiff to support its structure, no stiffness means need be used.

For purpose of illustration and not limitation, the internal diameter of the guiding introducer containing openings may vary from about 5 to about 8 "French". Such guiding introducer containing openings can accept ablation catheters from about 5 to about 8 French and appropriate guidewires. Obviously, if larger or smaller ablation catheters are used in conjunction with the guiding introducer containing openings, modifications in size or shape can be made to the guiding introducer containing openings.

The guiding introducer containing openings can be generally straight or it can be formed into a precurved shape.

The shape of the guiding introducer containing openings may be such as to permit the openings of the guiding introducer containing openings to rest against the cardiac tissue during the ablation procedure. The choice of possible shapes for the guiding introducer containing openings includes any of the shapes disclosed, for example in U.S. Pat. Nos. 5,427,119, 5,497,774, 5,575,766 and 5,564,440.

The ablation catheter that is utilized with the guiding introducer containing openings may be a conventional steerable ablation catheter or an ablation catheter which does not have steering capability. In a preferred embodiment, a steerable catheter, such as a Livewire® ablation catheter produced by Daig Corporation, is utilized.

Variations in size and shape of the guiding introducer containing openings are also intended to encompass pediatric uses, although the preferred uses are for adult human hearts. It is well recognized that pediatric uses may require reductions in size of the various sections of the guiding introducer containing openings, in particular the first section, but without any significant modification to the overall shape of the guiding introducer containing openings. In addition, variations in size or shape of the guiding introducer containing openings or ablation catheter are also intended to encompass the specialized situations that sometimes occur in patients with enlarged and rotated hearts.

Figure 9:
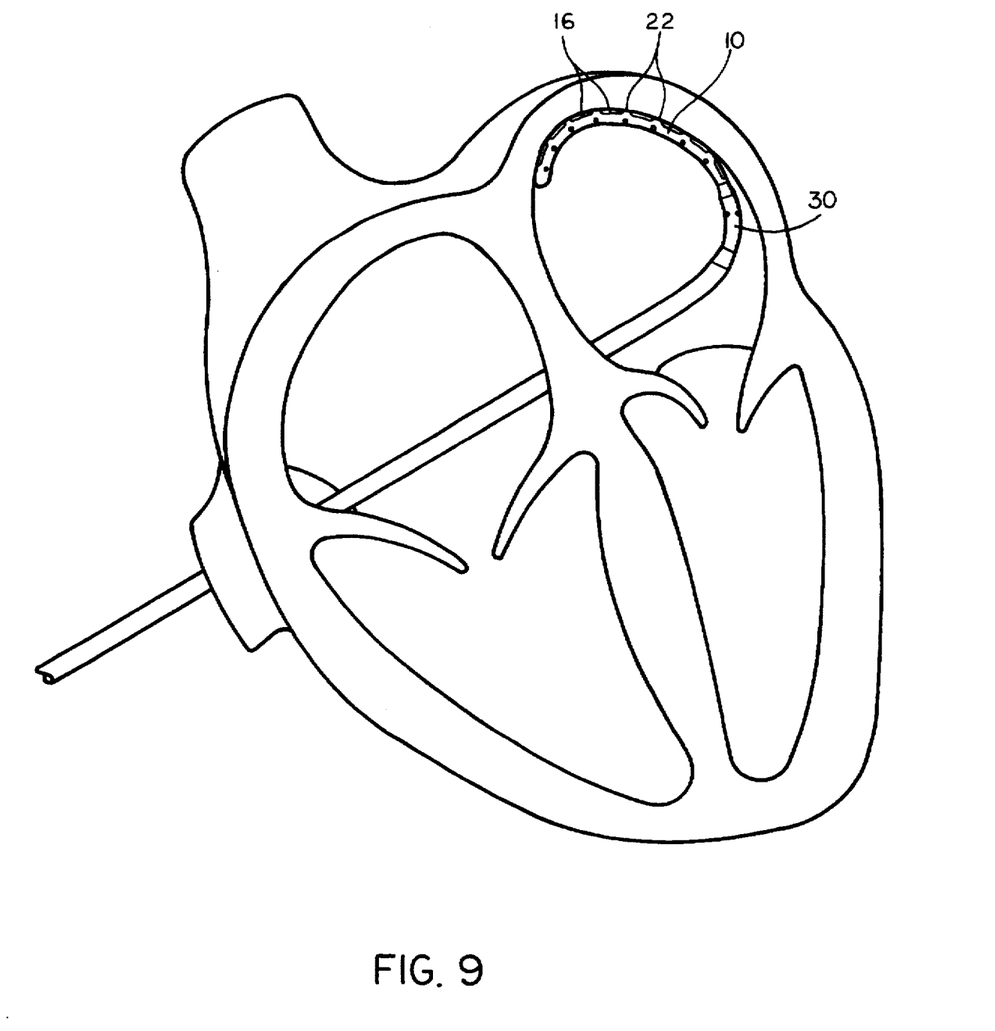
FIG. 9 is a cutaway view of the human heart showing the guiding introducer containing openings placed within the lumen of a shaped sheath in position in the left atrium for performing an ablation procedure.

In operation, a modified Seldinger technique is normally used for the insertion of the guiding introducer containing openings and ablation catheter into the body. Using this procedure, a small skin incision is made at the appropriate location to facilitate the catheter passage. Subcutaneous tissue is then dissected, followed by a puncture of the vessel with an appropriate needle with stylet positioned at a relatively shallow angle. The needle is then partially withdrawn and reinserted at a slightly different angle into the vessel making sure that the needle remains within the vessel. The soft flexible tip of an appropriately sized guidewire is then inserted through, and a short distance beyond, the needle into the vessel. Firmly holding the guidewire in place, the needle is removed. The guidewire is then advanced through the vessel into the appropriate chamber of the heart. For example, if the ablation procedure is to occur in the right atrium, the guidewire may be advanced into the right femoral vein through the vena cava into the right atrium. A shaped sheath or pair of such shaped sheaths (30), such as the shaped sheaths distributed by Daig Corporation and disclosed, for example, in U.S. Pat. Nos. 5,575,766, 5,427, 119, 5,497,774 and 5,564,440, with appropriate dilator is then advanced into the right atrium. While it is preferred that a shaped sheath be used with the guiding introducer containing openings, it is not mandatory. For example, the guiding introducer containing openings may contain its own distinct shape at its distal end which will permit it to be placed in the precise location necessary for the ablation procedure without the necessity of using a shaped sheath. However, in a preferred embodiment, a shaped sheath is used with the guiding introducer containing openings. With the shaped sheath (30) in place, the guiding introducer with openings (10) is advanced within the shaped sheath. It is important that the lumen of the guiding introducer containing openings be filled either with a removable obturator or with the ablation catheter. Preferably, the ablation catheter (18) and the guiding introducer containing openings (10) generally form an assembly to be advanced together within the shaped sheath (30) into the heart chamber chosen. The electrodes for sensing and ablation of the ablation catheter should rest at or near the distal tip of the guiding introducer containing openings. See FIG. 8. If necessary, the catheter containing electrodes which preferably is a steerable catheter, can steer the assembly to the precise location necessary for the sensing and ablation procedures to occur. See FIG. 9. (This Figure shows the guiding introducer containing openings in position for an ablation procedure in the left atrium.) In addition, fluoroscopy can be used to assist in the placement of the assembly.

In order to perform the ablation procedure, it is preferable that the guiding introducer containing openings (10) be anchored in place in the heart by pressing its distal tip (24) against cardiac tissue. The openings (16) of the guiding introducer containing openings are then pressed against the cardiac tissue at the appropriate location for the ablation procedure. See FIG. 9.

In order to perform the ablation procedure, the tip electrode (20) of the ablation catheter (18) is preferably placed adjacent to the distal-most opening (16) of the guiding introducer containing openings (10). As stated above, it is not critical that the ablating electrode and one of the openings (16) be perfectly aligned. Adequate lesion formation can occur where the ablating electrode is extended across the bridge (21) between two separate openings. Thus, the actual ablation procedure may occur through one or a pair of adjacent openings. Sufficient energy is then introduced to the ablating tip electrode (20) of the ablation catheter to ablate that particular location. In order to form a linear ablation lesion, the tip electrode (20) is then partially withdrawn to the next opening in the guiding introducer containing openings (10) where the ablation procedure is repeated. Depending upon the length of the lesion that is required, the tip electrode (20) of the ablation catheter (18) can be further withdrawn to create additional lesions until the lesion formed is of adequate length and depth. If preferred, the tip electrode (20) of the ablation catheter can then be returned to its original position opposite the distal-most opening of the guiding introducer containing openings and the ablation procedure repeated. In practice, it is common for the ablation procedure to be repeated as many as five times to insure formation of an adequate linear track. Sensing electrodes may be utilized during the ablation procedure to sense whether the cardiac arrhythmia has been eliminated. Once it has been determined that an adequate lesion has been formed, the guiding introducer containing openings, the shaped sheath and the ablation catheter are removed.

By use of the ablation catheter (18) with the guiding introducer containing openings (10) in coordination with fluoroscopic viewing, the distal portion of the guiding introducer containing openings can be manipulated to direct the ablating electrode of the mapping and/or ablation catheter to the specific location necessary for the ablation procedure. In addition, by providing sufficient rigidity and support, as the guiding introducer containing openings is held in place against the cardiac tissue, the guiding introducer containing openings creates a secure platform to permit an adequate ablation procedure to be performed. The structure of the guiding introducer containing openings, the retention of the ablation catheter within the guiding introducer containing openings, and the shape of the shaped sheath also assist in precise placement of the ablation catheter. This precise placement of the ablation catheter tip in the correct location is important as there will be no dilution of energy delivered due to the unfocused energy being dissipated over the entire cardiac chamber and lost in the circulating blood by a constantly moving tip of the ablating catheter. This process permits a significantly reduced usage of energy during the ablation procedure. Further, the time used to perform the ablation procedure is significantly reduced over procedures where no guiding introducer containing openings is used. In addition, by this ablation procedure the same types of destruction of the discrete tracks can be achieved as has been accomplished, for example, in surgical applications and other ablation procedures.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A system for linear ablation comprising a guiding introducer containing openings and an ablation catheter with electrodes, wherein the guiding introducer comprises a first proximal and a second distal section, wherein the first proximal section comprises an elongated section containing a lumen, wherein the second distal section comprises an introducer section containing a plurality of openings, wherein the openings are of sufficient size to permit ablation of cardiac tissue through the openings by the electrodes of the ablation catheter, wherein the openings feature a width and a length, and wherein the ablation catheter features a diameter which is greater than the width or length of the openings, such that the ablation catheter remains inside the lumens of the first and second sections of the guiding introducer during the ablation of cardiac tissue.

2. The system of claim 1, wherein the guiding introducer contains an inner diameter and wherein the width of the openings extends around the circumference of the guiding introducer, and the length of the openings extends longitudinally along the second distal section of the guiding introducer.

3. The system of claim 2, wherein the width of the openings is from about 25 to about 90 percent of the inner diameter of the guiding introducer.

4. The system of claim 2, wherein the length of the openings is from about 3 to about 10 mm.

5. The system of claim 2, wherein the length of the openings is from about 25 to about 90 percent of the inner diameter of the guiding introducer.

6. The system of claim 1, wherein the openings are in the form of a circle.

7. The system of claim 2, wherein the second distal section contains a distal tip.

8. The system of claim 7, wherein the distal tip contains a hole having a diameter which is less than about 90 percent of the inner diameter of the guiding introducer.

9. The system of claim 1, wherein the guiding introducer contains a series of apertures located from about 45 to about 180 degrees axial from the openings.

10. The system of claim 9, wherein the guiding introducer contains three series of apertures, each located from about 90 to about 180 degrees axial from the openings.

11. The system of claim 1, wherein the first proximal section of the guiding introducer containing openings is braided.

12. The system of claim 1, wherein the second distal section contains a tip marker.

13. The system of claim 12, wherein the tip marker extends partially around the circumference of the guiding introducer.

14. The system of claim 1, wherein the second section of the guiding introducer is steerable by a steerable catheter.

15. The system of claim 1 wherein the electrodes of the ablation catheter contain an outside diameter, wherein the lumen of the distal second section has an inner diameter, and wherein the inner diameter of the second section is greater than the outside diameter of the ablation catheter.

16. The system of claim 1 wherein the ablation electrode is from about 2 to about 8 millimeters in length.

17. The system of claim 1 wherein the ablation catheter is a steerable catheter.

18. The system of claim 1 wherein the openings of the distal second section are generally contained within a linear line extending longitudinally along the second distal section of the guiding introducer.

19. A process for nonsurgical mapping and treatment of cardiac arrhythmia within a human heart using an ablation catheter and a lumened guiding introducer containing openings comprising introducing the guiding introducer containing openings into a chamber of the human heart, introducing into the lumen of the guiding introducer an ablation catheter wherein the ablation catheter contains an ablation electrode, extending the ablation electrode of the ablation catheter into the lumen of the guiding introducer, retaining the ablation catheter and ablation electrode within the guiding introducer, and ablating an area of the heart through the openings in the guiding introducer by use of the ablation electrode of the ablation catheter.

* * * * *